United States Patent [19]
Gaterud et al.

[11] Patent Number: 5,522,882
[45] Date of Patent: Jun. 4, 1996

[54] METHOD AND APPARATUS FOR BALLOON EXPANDABLE STENT-GRAFT DELIVERY

[75] Inventors: Mark T. Gaterud; Rajagopal R. Kowligi, both of Phoenix; Fariba Khalilifard; Christopher E. Banas, both of Mesa, all of Ariz.

[73] Assignee: Impra, Inc., Tempe, Ariz.

[21] Appl. No.: 327,195

[22] Filed: Oct. 21, 1994

[51] Int. Cl.$^6$ .................................................. A61F 2/06
[52] U.S. Cl. ................. 623/1; 606/192; 606/195; 606/108
[58] Field of Search ................. 623/1, 11; 606/192, 606/194, 195, 198, 108

[56] References Cited

U.S. PATENT DOCUMENTS

| | | | |
|---|---|---|---|
| 4,564,014 | 1/1986 | Fogarty et al. | 128/344 |
| 4,617,932 | 10/1986 | Kornberg | 128/334 R |
| 4,655,771 | 4/1987 | Wallsten | 623/1 |
| 4,705,517 | 11/1987 | DiPisa | 623/12 |
| 4,732,152 | 3/1988 | Wallsten et al. | 128/343 |
| 4,787,899 | 11/1988 | Lazarus | 623/1 |
| 4,830,062 | 5/1989 | Yammoto | 138/177 |
| 4,875,480 | 10/1989 | Imbert | 128/343 |
| 4,877,030 | 10/1989 | Beck | 128/343 |
| 4,878,906 | 11/1989 | Lindemann et al. | 623/1 |
| 4,950,227 | 8/1990 | Savin et al. | 623/1 |
| 4,955,899 | 9/1990 | Della Corna | 623/1 |
| 4,969,890 | 11/1990 | Sugita | 606/192 |
| 5,074,845 | 12/1991 | Miraki et al. | 606/194 |
| 5,078,726 | 1/1992 | Kreamer | 606/194 |
| 5,108,416 | 4/1992 | Ryan et al. | 606/194 |
| 5,116,318 | 6/1992 | Hillstead | 606/194 |
| 5,122,154 | 6/1992 | Rhodes | 606/198 |
| 5,123,917 | 6/1992 | Lee | 623/1 |
| 5,163,952 | 11/1992 | Froix | 623/1 |
| 5,197,952 | 3/1993 | Marcadis et al. | 606/194 |
| 5,275,622 | 1/1994 | Lazarus | 623/1 |
| 5,330,500 | 7/1994 | Song | 623/1 |
| 5,342,305 | 8/1994 | Shonk | 606/194 |
| 5,344,425 | 9/1994 | Sawyer | 606/198 |
| 5,360,403 | 11/1994 | Mische | 606/192 |
| 5,360,443 | 11/1994 | Barone et al. | 606/195 |
| 5,409,495 | 4/1995 | Osborn | 606/108 |

*Primary Examiner*—Mary Beth Jones
*Assistant Examiner*—Bruce E. Snow
*Attorney, Agent, or Firm*—David G. Rosenbaum

[57] ABSTRACT

A stent-graft delivery system which includes a catheter, an expandable balloon having non-tapered ends positioned near the distal end of the catheter, a stent circumferentially positioned around a center of the balloon, and a graft circumferentially positioned around the stent. The balloon configuration comprising non-tapered ends may be achieved by 1) preforming the balloon to the desired geometry which comprises substantially non-tapered ends; 2) positioning a non-compliant sheath over each of the ends of an existing balloon having tapered ends, or 3) invertedly attaching the first and second ends of a compliant tubular member to the catheter to form the desired balloon configuration. The desired balloon configuration is a balloon geometry which uniformly conforms to the geometry of the stent-graft assembly. A method for introducing the stent-graft delivery system into a blood vessel are also disclosed. The method includes inserting the stent-graft delivery system into the blood vessel, guiding the stent-graft assembly to the desired site, inflating the balloon of the balloon catheter, deflating the balloon, and withdrawing the catheter and expandable balloon. The stent-graft delivery systems are also suitable for introducing and delivering stents without grafts.

20 Claims, 3 Drawing Sheets

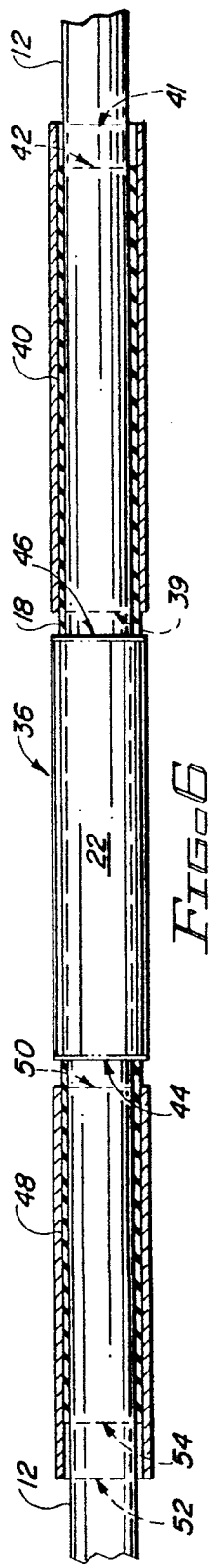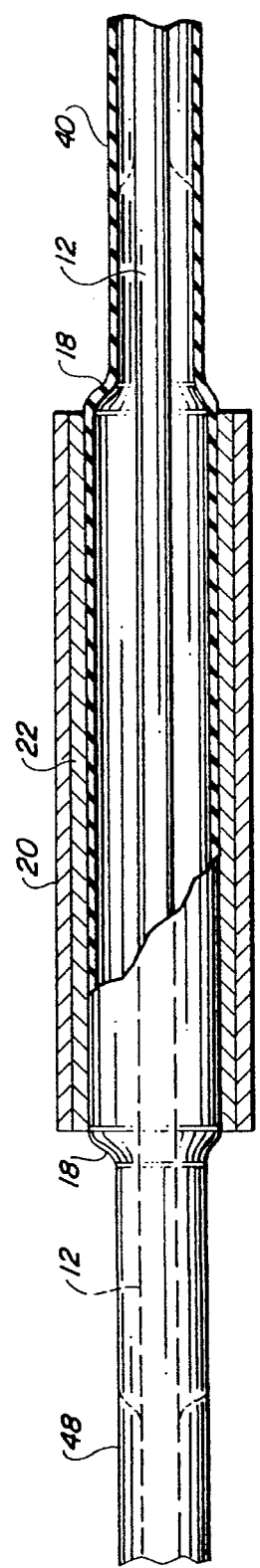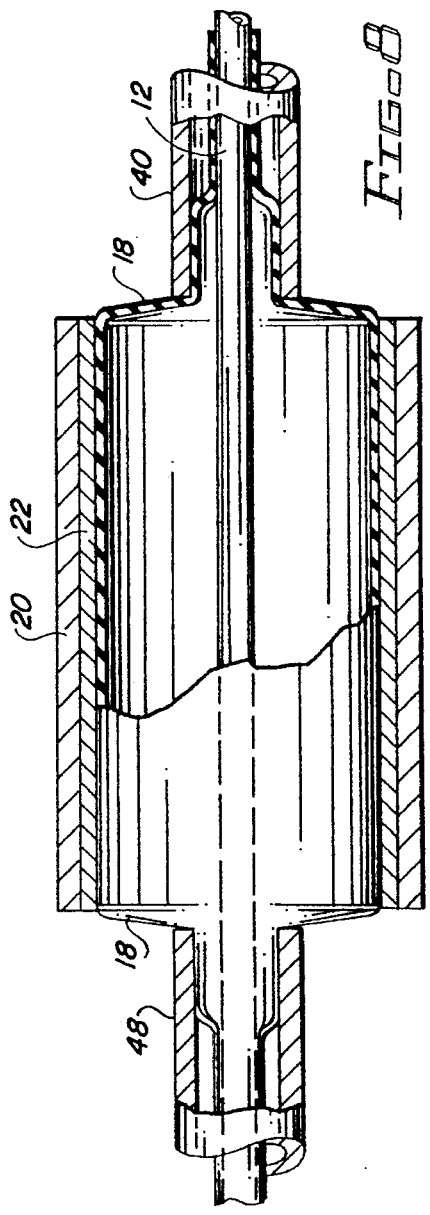

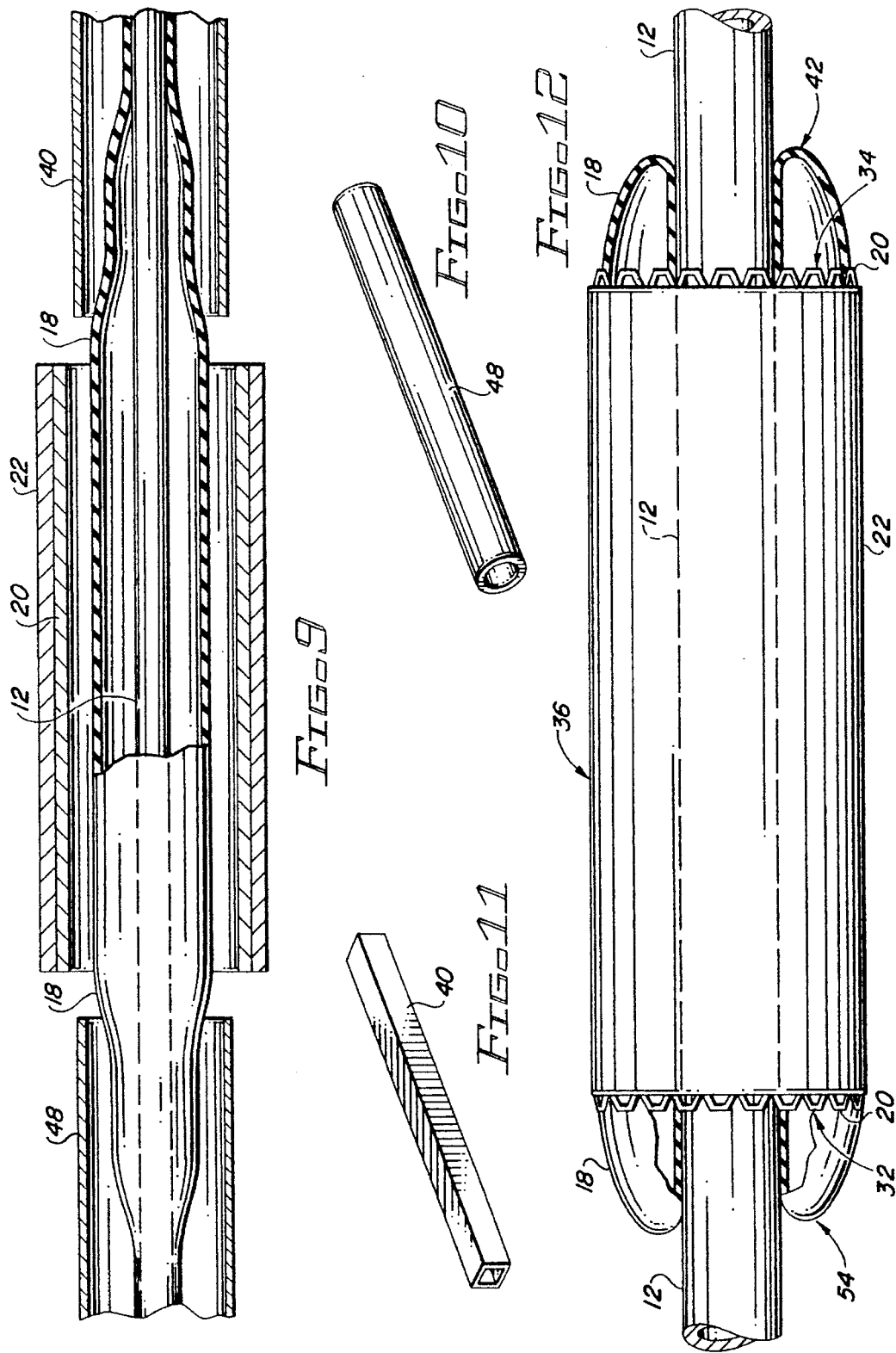

METHOD AND APPARATUS FOR BALLOON EXPANDABLE STENT-GRAFT DELIVERY

BACKGROUND OF THE INVENTION

The present invention generally relates to a method and apparatus for a balloon expandable stent-graft delivery system. More particularly, the present invention relates to a method and apparatus for introducing and securing a stent-graft assembly within a blood vessel using a balloon catheter which allows for the uniform radial expansion of the stent-graft assembly.

Clinical trials have demonstrated the effectiveness and safety of stents for recanalization of obstructed or completely occluded blood vessels. Palmaz, et al., "Stenting of the iliac arteries with the Palmaz stent: Experience from a multicenter trial." 15 *Cardiovascular Interventional Radiology* 291 (1992); Carrasco, et al., "Use of the Gianturco self-expanding stent in stenoses of the superior and inferior venae cavae." 3 Journal of Vascular and *International Radiology* 409 (1992). Stents are generally introduced into a blood vessel by the use of a catheter.

Several balloon catheter systems for introducing and delivering a stent into a blood vessel are known in the field of art relating to stents. For example, U.S. Pat. No. 5,108,416 discloses a stent introducer system comprising a balloon catheter having a stent surrounding the balloon portion of the catheter. Flexible end caps having mounting sleeves are affixed to the catheter adjacent the ends of the balloon to retain the stent in its position during inflation of the balloon. Inflation of the balloon causes the end caps to move axially and radially away from the stent, thereby releasing the stent. Another stent delivery system, described in U.S. Pat. No. 4,950,227, includes a catheter having an expandable distal portion, a stent positioned around the distal portion, and an expandable sleeve positioned around the catheter having one end affixed to the catheter and the other end overlapping the stent. Expanding the distal portion of the catheter causes the stent to expand and the sleeve to slide axially away from the stent thereby releasing the stent.

The use of stents in combination with polytetrafluoroethylene (PTFE) or polymer grafts are particularly useful in treating focal vascular lesions such as aneurysms, pseudoaneurysms and arteriovenous fistulas and atherosclerotic and occlusive diseases with both discrete and diffuse lesions by functioning to exclude the abnormal vascular lumen. A PTFE graft is radially expandable if a coaxial balloon is inflated within its lumen. However, physical problems arise when expanding a stent-PTFE graft assembly with a balloon catheter where the PTFE graft material is co-axially placed over the stent.

The length of the balloon chosen for expanding the stent-graft assembly is critical. If an excessively long balloon is chosen, the inflation of the balloon will result in a "dumb-bell" shaped expansion. The "dumb-bell" shaped expansion causes the ends of the stent to flare outward thereby causing the graft to compress in a longitudinal direction and bunch up in the middle of the stent.

Ideally, prior studies have indicated that the balloon length should be less than the length of the stent-graft assembly and have short tapered ends. This shorter balloon expands the stent-graft from the center out and produces an expanded stent-graft assembly with tapered ends. The balloon is then deflated, repositioned, and reinflated to expand the tapered ends of the partially expanded stent-graft assembly. However, this procedure could lead to balloon ruptures or snags due to a lack of uniform and continuous expansion and the need to reposition the balloon to obtain a uniform expansion of the stent-graft assembly.

Further, if used for expanding a stent-graft assembly, the balloon catheter systems for introducing and delivering stents which are currently known would not overcome the physical expansion problems involved in expanding the stent-graft assembly. More specifically, with reference to U.S. Pat. Nos. 5,108,416 and 4,950,227, described above, the end caps and expandable sleeves which would overlap the ends of the stent-graft assembly during the expansion process would produce an expanded stent-graft assembly having tapered ends. These tapered ends would then require additional expansion in order to obtain an expanded stent-graft assembly having a uniform geometry.

Accordingly, there is a need for a method and apparatus for introducing and delivering a stent-graft assembly which is capable of performing a uniform and continuous radial expansion of the stent-graft assembly. There is also a need for a method and apparatus for introducing and delivering a stent-graft assembly which is capable of expanding the stent-graft assembly without incurring substantial retraction of the graft over the stent.

SUMMARY OF THE INVENTION

It is a principal object of the present invention to provide a balloon expandable stent-graft delivery system which is capable of producing a continuous uniform expansion of the stent-graft assembly.

It is a further object of the present invention to provide a balloon expandable stent-graft delivery system which expands a stent-graft assembly from the middle section of the stent-graft assembly.

It is a still further object of the present invention to provide a balloon expandable stent-graft delivery system wherein the balloon contained within the system comprises non-tapered ends in its expanded state.

It is a still further object of the present invention to provide an extended graft delivery system wherein the balloon contained within the system is parallel with the stent-graft assembly along its longitudinal axis from an unexpanded to an expanded state.

It is yet a further object of the present invention to provide an expanded stent-graft assembly produced from a balloon expandable stent-graft delivery system which exhibits uniform radial expansion throughout without tapered or flared ends.

According to a broad aspect of the invention, there is provided a balloon expandable stent-graft delivery system which includes a catheter, an expandable balloon having non-tapered ends positioned near the distal end of the catheter, a stent circumferentially positioned around a center of the balloon, and a graft circumferentially positioned around the stent. The balloon configuration comprising non-tapered ends may be achieved by positioning a non-compliant sheath over each of the ends of an existing balloon having tapered ends. Alternatively, the first and second ends of a compliant tubular member may be invertedly attached to the catheter to form the desired balloon configuration.

The present invention also provides a balloon expandable stent-graft delivery system which includes a balloon catheter having an expandable balloon, a stent circumferentially positioned around a center of the balloon, a graft circumferentially positioned around the stent, and at least one sheath positioned over a tapered end of the expandable balloon such that it does not overlap the stent. Preferably, another sheath is positioned similarly over the balloon's remaining tapered end. The sheath may comprise any number of geometrical configurations including, but not limited to, a cylindrical rod configuration or a rectangular shaft configuration. The sheath may be comprised of a heat shrinkable tubing, a metal tubing, or a plastic tubing, or any other restraining means such as a wrap.

Alternatively, the balloon expandable stent-graft delivery system may comprise a catheter having proximal and distal ends, an expandable balloon attached near the distal end of the catheter wherein the balloon comprises first and second ends and at least one of the balloon's ends is invertedly attached to the catheter, a stent positioned circumferentially around the balloon, and a graft positioned circumferentially around the stent.

The balloon expandable stent-graft delivery system may also comprise a catheter having proximal and distal ends, an expandable balloon having first and second ends wherein one or both of these ends is preformed such that it exhibits a non-tapered end, a stent positioned circumferentially around the balloon, and a graft positioned circumferentially around the stent. The preformed end of the balloon may be formed by molding or any other means which is known for forming or manufacturing balloons or other compliant, expandable material which can function as a balloon. If only one end of the balloon is preformed, the other non preformed, tapered end of the balloon may be covered by a sheath or inverted in order to achieve a non-tapered end.

There is also provided a method for introducing a stent-graft assembly into a blood vessel comprising the steps of:
  a) providing a balloon expandable stent-graft delivery system comprising:
    a catheter having proximal and distal ends thereof;
    an expandable balloon attached near the distal end of said catheter wherein said balloon comprises an interior surface, an exterior surface, and first and second ends, said first and second ends being substantially non-tapered upon expansion of said balloon from a first unexpanded diameter to a second larger diameter;
    a stent having an interior surface, an exterior surface, and first and second ends thereof wherein said stent is positioned around said expandable balloon; and
    a graft having an interior surface, an exterior surface, and first and second ends thereof wherein said graft is positioned around said stent such that said stent is concentrically contained within said graft;
  b) inserting the balloon expandable stent-graft delivery system into the blood vessel;
  c) guiding the stent-graft assembly to a desired site;
  d) inflating the expandable balloon to the second larger diameter to seat the stent-graft assembly within the blood vessel at the desired site;
  e) deflating the balloon; and
  f) withdrawing the catheter and expandable balloon from the blood vessel.

These and other objects, features and advantages of the present invention will become more apparent to those skilled in the art from the following more detailed description of the preferred embodiments taken with reference to the accompanying drawings.

BRIEF DESCRIPTION OF THE DRAWINGS

FIG. 6 is a partial isometric view, partially shown in longitudinal section, of the balloon expandable stent-graft delivery system, in an unexpanded state, having two sheaths near the ends of the stent-graft assembly.

FIGS. 7–8 are partial isometric views, partially shown in longitudinal section, showing the simultaneous expansion of the balloon expandable stent-graft delivery system of FIG. 1.

FIG. 9 is a partial isometric view, partially shown in longitudinal section, of the balloon expandable stent-graft delivery system, in a partially deflated state.

FIG. 10 is a perspective view of the sheath comprising part of the balloon expandable stent-graft delivery system of the present invention.

FIG. 11 is a perspective view of another embodiment of the sheath comprising part of the balloon expandable stent-graft delivery system of the present invention.

FIG. 12 is a side elevational view, partially shown in longitudinal section, of another embodiment of the balloon expandable stent-graft delivery system of the present invention.

DETAILED DESCRIPTION OF THE PREFERRED EMBODIMENTS

Figure 1:
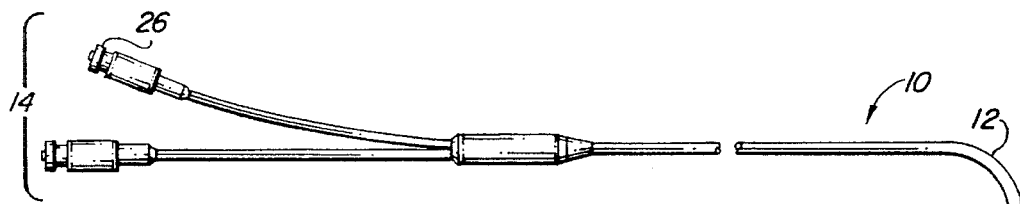
FIG. 1 is a perspective view of a balloon expandable stent-graft delivery system in accordance with the present invention prior to expansion of the stent-graft assembly.

As shown in FIG. 1, the balloon expandable stent-graft delivery system 10 of the present invention generally comprises a catheter 12 having a proximal end 14 and a distal end 16, an expandable balloon 18 attached to the catheter 12 near the distal end 16 of the catheter 12, a stent 20 positioned around the expandable balloon 18, a graft 22 positioned around the stent 20 such that the graft 22 is concentrically contained within the stent 20, and at least one sheath 24 positioned over the expandable balloon 18 such that it is adjacent to at least one end of the stent 20 but does not overlap the stent 20. The expandable balloon 18 is attached to the catheter 12 and is capable of expanding from an unexpanded state to an expanded state by inflating the expandable balloon 18. The expandable balloon 18 can be inflated by pumping or injecting gas or fluid into a port 26 at the proximal end 14 of the catheter 12.

Figure 2:
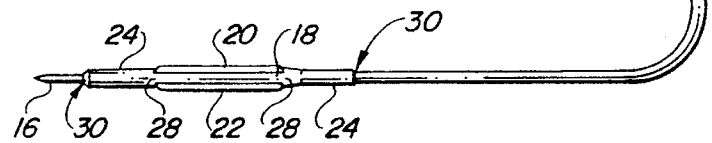
FIG. 2 is a side elevational view of a portion of the balloon expandable stent-graft delivery system showing the stent and one sheath positioned over the expandable balloon.

A partial section of the balloon expandable stent-graft delivery system 10 showing the stent 20 and a sheath 24 positioned over the expandable balloon 18 in an unexpanded state is shown in FIG. 2. The sheath 24 comprises a tubular configuration having first and second ends 28, 30 and is preferably comprised of a heat shrinkable tubing, a metallic tubing, or a plastic tubing, all of which are substantially non-compliant. The sheath 24 is preferably capable of minimal expansion. The stent 20 is cylindrical in shape and has first and second ends 32, 34. The stent 20 preferably comprises a metal mesh or metal weave such as evidenced by the "PALMAZ" stent. Within the delivery system 10, the first end 28 of the sheath 24 is positioned adjacent to the second end 34 of the stent 20 without overlapping the stent 20. Preferably, the balloon expandable stent-graft delivery system 10 comprises two sheaths, one positioned on each side of the stent 20. Accordingly, the first end 28 of another sheath 24 is preferably positioned adjacent to the first end 32 of the stent 20 without overlapping the stent 20. This positioning of the sheaths 24 constrains the ends of the expandable balloon 18 thereby "squaring off" the ends of the expandable balloon 18 by inhibiting inflation of the tapered ends of the expandable balloon 18 which are attached to the catheter 12. This positioning constrains the balloon 18 to an expandable "working length" which is substantially equal to the length of the stent-graft assembly 36.

Figure 3:
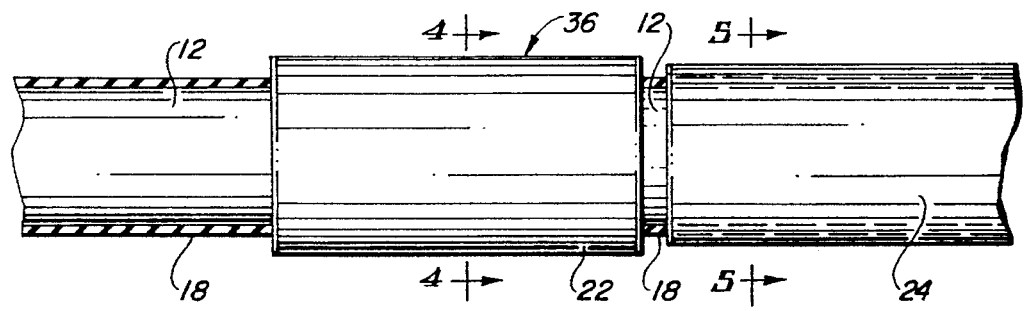
FIG. 3 is a side elevational view of a portion of the balloon expandable stent-graft delivery system showing the stent-graft assembly and one sheath positioned over the expandable balloon.

FIG. 3 illustrates the graft 22 positioned coaxially over the stent 20. Both the stent-graft assembly 36 and the sheath 24 are positioned over the expandable balloon 18 of the balloon expandable stent-graft delivery system 10. The graft 22 is preferably comprised of PTFE or other polymeric material suitable for vascular grafts and able to be radially expanded. The expandable balloon 18 and the catheter 12 are generally known in the art as a "balloon catheter" and those types of balloon catheters generally known in the art are herein incorporated by reference as suitable balloon catheters for comprising the balloon and catheter components of the present invention. The stent-graft assembly 32, the sheath 24 and the expandable balloon 18 are all shown in their unexpanded states in FIG. 3.

Figure 4:
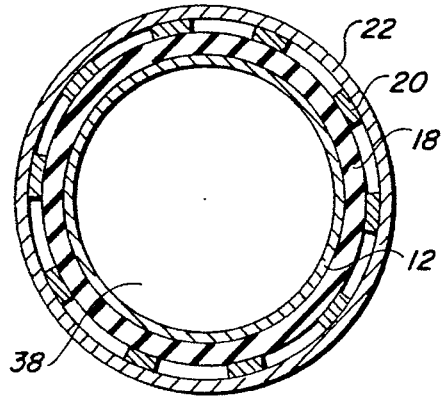
FIG. 4 is a cross sectional view taken along lines 4—4 of FIG. 3.
Figure 5:
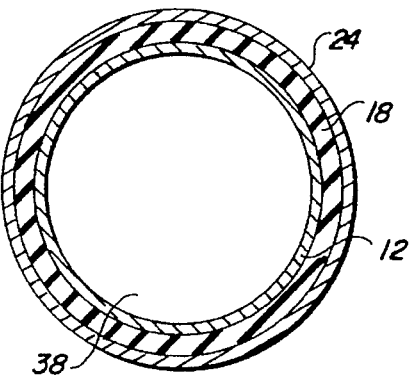
FIG. 5 is a cross-sectional view taken along lines 5—5 of FIG. 3.

A cross-section of the stent-graft assembly 36 mounted on the balloon catheter prior to expansion is shown in FIG. 4. The expandable balloon 18 is on the exterior surface of, and surrounds a length of the exterior surface of, the catheter 12. The graft 22 is placed over the stent 20 such that the graft is concentrically contained within the stent 20 thereby forming the graft-stent assembly 36. The entire graft-stent assembly 36 is placed over the expandable balloon 18. The lumen 38 of the catheter 12 may be filled with gas or fluid in order to inflate the expandable balloon 18. At least one opening must pass through the wall of the catheter 18 to enable the contents of the lumen 38 to pass through the catheter wall and fill the expandable balloon 18. FIG. 5 is a cross-section taken along lines 5—5 of FIG. 3 showing the sheath 24 mounted on the balloon catheter. The expandable balloon 18 surrounds a length of the exterior surface of the catheter 12. The sheath 24 is positioned concentrically around one end of the expandable balloon 18 such that it covers at least one end of the balloon and also sits adjacent to one end of the stent 20 without overlapping the stent 20.

FIG. 6 illustrates the balloon expandable stent-graft delivery system in its unexpanded state having a sheath positioned near each end of the stent-graft assembly. A first sheath 40 having first and second ends 39, 41 is pushed over the distal end of the catheter 12 and positioned around the proximal end 42 of the expandable balloon 18 such that the second end 41 of the first sheath 40 completely overlaps that area where the proximal end 42 of the balloon 18 is attached to the catheter 12. The first end 39 of the first sheath 40 is designed to terminate at a point somewhere between the middle and proximal end 42 of the balloon 18 depending on the length of the stent-graft assembly 36 which is to be expanded via the balloon expandable stent-graft delivery system 10. Alternatively, the first sheath 40 may extend along the entire remaining length of the catheter 12 such that the first end 41 of the first sheath 40 terminates at the proximal end of the catheter 12. The first sheath 40 may be affixed to the catheter 12 or may be slidably manipulative along the length of the catheter shaft.

The graft 22 is placed around the stent 20 such that the stent 20 is concentrically contained within the graft 22 and the stent-graft assembly 36 is slid or pushed over the distal end of catheter 12 subsequent to the loading of the first sheath 40 onto the balloon catheter. The stent-graft assembly 36 has first and second ends 44, 46 and is positioned such that its second end 46 is located adjacent to the first end 39 of the first sheath 40. The stent-graft assembly 36 is equal to or shorter in length than the expandable balloon 18 and is positioned circumferentially around the center of the expandable balloon 18.

After the stent-graft assembly 36 is positioned around the expandable balloon 18, a second sheath 48 having first and second ends 50, 52 is pushed over the distal end 16 of the catheter 12. The second sheath 48 is positioned such that its first end 50 is located adjacent to the first end 44 of the stent-graft assembly 36 and its second end 52 completely overlaps that area where the distal end 54 of the expandable balloon 18 is attached to the catheter 12. The first and second sheaths 40, 48 do not overlap any portion of the stent-graft assembly. The first and second sheaths 40, 48 may be affixed to the catheter 12 with glue or any other suitable attachment means.

The beginning inflation of the expandable balloon 18 is shown in FIG. 7. The first and second sheaths 40, 48 act to constrain the proximal and distal end areas of the balloon 18 from inflating thereby forcing only the mid-portion of the balloon 18 to radially expand. Expansion of the mid-portion of the expandable balloon 18 results in the expansion of the stent-graft assembly 36 in a uniform manner. FIG. 8 illustrates the expandable balloon stent-graft delivery system 10 in its expanded state. The first and second sheaths 40, 48 have constrained the proximal and distal ends of the balloon 18 from expanding during inflation thereby eliminating the tapered ends of the balloon 18. This non-tapered balloon configuration forces a continual uniform expansion of the stent-graft assembly 36 thereby avoiding contraction of the graft toward its center during expansion by holding the graft 22 in place on the stent 20 during expansion of the stent-graft assembly 36.

After expansion of the stent-graft assembly 36 is complete, the expandable balloon 18 is deflated as shown in FIG. 9. The balloon catheter containing the sheaths 40, 48 is removed by sliding it out from the expanded stent-graft assembly 36.

Other embodiments for the first and second sheaths 40, 48 are contemplated by the present invention. More particularly, FIGS. 10 and 11 illustrates sheath configurations for use with the balloon expandable stent-graft delivery system 10 of the present invention. FIG. 11 shows a hollow rectangular shaped shaft which could function as a sheath, as previously described, given a suitable material for its composition. However, any sheath geometry which provides for maximum inner surface area contact with the balloon is contemplated by the invention. Suitable materials for the sheaths 40, 48 include polyethylenes, polypropylenes, polyamides, polyimides, PETG, any rigid plastic material, polycarbonates, metal, ceramics, stainless steel, gold, platinum, any other rigid non-compliant material, or any other restraining means such as a wrap.

Referring now to FIG. 12, there is shown an alternative embodiment of the balloon expandable stent-graft delivery system 10 of the present invention in an expanded state. The alternative embodiment comprises a catheter 12 having proximal and distal ends, an expandable balloon 18 having proximal and distal ends 42, 54 which are invertedly attached to the exterior surface of the catheter 12, a stent 20 having first and second ends 32, 34 which is positioned circumferentially about the expandable balloon 18, and a graft 22 positioned circumferentially about the stent 20. The inverted attachment of the proximal and distal ends 42, 54 of the expandable balloon 18 may be achieved in a number of ways. For example, the proximal and distal ends of a cylindrical tube composed of suitable balloon material may be turned inward and then glued or affixed to the outer surface of the catheter 12. Alternatively, inverted collar members may be placed around the catheter such that the proximal and distal ends of the balloon may be affixed to the inverted collars which effectively act as a spacer between the catheter and the balloon, thereby "squaring off" the balloon.

The inverted attachment of the proximal and distal ends 42, 54 of the balloon 18 to the catheter 12 result in a non-tapered balloon configuration upon inflation of the balloon. As previously stated, the untapered balloon configuration is desirable because it results in a continuous uniform expansion of the stent-graft assembly 36. A graft length may be specifically selected to ensure that slight shrinkage of the graft will produce minimal stent protrusions beyond the length of the graft, as shown in FIG. 12, to assist in anchoring the stent-graft assembly 36 to the blood vessel. Alternatively, if no stent protrusions are desired, a pre-expansion graft sufficiently longer than or equal to the length of the stent can be chosen for expansion.

It should be noted that all previously described embodiments of the balloon expandable stent-graft delivery system are equally applicable and effective for use in expanding stents alone. Further, the above described embodiments of the present invention are preferable for expanding stents over those apparata and methods currently known in the art in that the present invention provides for continuous uniform expansion of the stent while avoiding the formation of tapered ends or ends which flare.

Laboratory experiments were carried out to test the uniform and continual expansion of a stent-graft assembly using a rectangular balloon configuration. The experiments are explained in more detail by the following examples:

EXAMPLE 1

A 3 millimeter internal diameter (ID) thin wall PTFE graft was loaded on a P-308 "PALMAZ" stent with a slight overlap over the stent to compensate for graft shortening at expansion. The graft-stent assembly was loaded on a 10×40 millimeter (mm) balloon catheter. Stainless steel tubing sections were positioned over the tapered ends of the balloon. The balloon was expanded in a 37° C. water bath.

RESULTS: 8 atmospheres (ATM) of pressure was required to fully expand the stent-graft assembly. The middle of the stent-graft assembly expanded prior to its ends.

EXAMPLE 2

A 3 millimeter ID graft was fitted over a P-308 "PALMAZ" stent. The stent-graft assembly was loaded on a 10×40 mm balloon catheter between sections of stainless steel tubing which covered the tapered ends of the balloon such that the stainless steel tubing was positioned adjacent to the stent-graft assembly. The stent-graft assembly was expanded in a 37° C. water bath at a beginning pressure of 4 ATM.

RESULTS: The stent-graft assembly was fully expanded at 10 ATM. Expansion occurred from the middle of the stent-graft assembly. 4 ATM were required to fully expand balloon without the load.

| Pressure Supplied | Outer Diameter of Stent-Graft Assembly |
| --- | --- |
| 6 ATM | 9.53 mm |
| 8 ATM | 9.92 mm |
| 10 ATM | 9.92 mm |

The above examples illustrate that a balloon in a balloon catheter, when manipulated to achieve a "rectangular" configuration upon expansion, will produce uniform radially expanded stent-graft assemblies.

While the preferred embodiments of the invention have been shown and described, it will be apparent to those skilled in the art that various changes and modifications may be made without departing from the true spirit and scope of the present invention. Therefore, the invention should not be construed as limited to the specific forms shown and described, but instead is as set forth in the following claims.

We claim:

1. A balloon expandable stent-gaff delivery system comprising:
    a) a catheter having proximal and distal ends thereof;
    b) an expandable balloon attached near the distal end of said catheter wherein said balloon comprises an interior surface, an exterior surface, and first and second ends, said first and second ends being substantially non-tapered upon expansion of said balloon from a first unexpanded diameter to a second larger diameter;
    c) a stent having an interior surface, an exterior surface, and first and second ends thereof wherein said stent is positioned around said expandable balloon;
    d) a graft having an interior surface, an exterior surface, and first and second ends thereof wherein said graft is positioned around said stent such that said stent is concentrically contained within said graft; and
    (e) a substantially non-compliant sheath positioned over each of said first and second ends of said expandable balloon, wherein each of said sheaths is positioned adjacent to one of said first and second ends of said stent, respectively, without overlapping onto or underlying any region of said stent.

2. The balloon expandable stent-graft delivery system of claim 1 wherein said balloon is substantially parallel along its longitudinal axis upon expansion.

3. The balloon expandable stent-graft delivery system of claim 1 wherein the exterior surface of said balloon in its expanded state is substantially parallel in length along the entire interior surface of the graft.

4. The balloon expandable stent-graft delivery system of claim 1 wherein said sheaths are substantially non-compliant.

5. The balloon expandable stent-graft delivery system of claim 1 wherein said expandable balloon, in said balloon's expanded state, and said stent are equal in length.

6. The balloon expandable stent-graft delivery system of claim 1 wherein said graft and said stent are equal in length.

7. The balloon expandable stent-graft delivery system of claim 1 wherein said stent is equal to or shorter than a length of said expandable balloon.

8. The balloon expandable stent-graft delivery system of claim 1 wherein said non-tapered first and second ends of said expandable balloon are invertedly attached to said catheter.

9. The balloon expandable stent-graft delivery system of claim 8 wherein said expandable balloon, in said balloon's expanded state, and said stent are equal in length.

10. A balloon expandable stent-graft delivery system comprising:
   a) a catheter having proximal and distal ends thereof and an expandable balloon attached near the distal end of said catheter wherein said expandable balloon has proximal and distal ends thereof and is capable of being expanded from a first unexpanded diameter to a second larger diameter;
   b) a stent having first and second ends wherein said stent is positioned around said expandable balloon;
   c) a graft positioned around said stent such that said stent is concentrically contained within said graft;
   d) a first substantially radially non-compliant sheath positioned over a distal end of the expandable balloon laterally adjacent and positionally fixed relative to a first of said stent when said expandable balloon is in its first unexpanded diameter and in its second expanded diameter and;
   e) a second substantially radially non-compliant sheath positioned over a proximal end of the expandable balloon and laterally adjacent to a second end of said stent when said expandable balloon is in its first unexpanded diameter and in its second expanded diameter.

11. The balloon expandable stent-graft delivery system of claim 10 wherein said stent is equal to or shorter than a length of said expandable balloon.

12. The balloon expandable stent-graft delivery system of claim 10 wherein said graft is a vascular graft comprising expanded polytetrafluoroethylene.

13. The balloon expandable stent-graft delivery system of claim 10 wherein said first and second substantially non-compliant sheaths each further comprise at least one of a heat shrinkable tubing, a metal tubing, a plastic tubing, and a restraining wrap.

14. The balloon expandable stent-graft delivery system of claim 10 wherein second substantially non-compliant sheath extends along a length of said catheter to the proximal end of said catheter such that it is slidably manipulative along said length of said catheter.

15. A balloon expandable stent-graft delivery system comprising:
   a) a catheter having proximal and distal ends thereof,
   b) an expandable balloon attached near the distal end of said catheter wherein said balloon has first and second ends and at least one of said ends is preformed to configure a non-tapered end;
   c) a stent having an interior surface, an exterior surface, and first and second ends thereof wherein said stent is positioned around said expandable balloon;
   d) a graft having an interior surface, an exterior surface, and first and second ends thereof wherein said graft is positioned around said stent such that said stent is concentrically contained within said graft; and
   (e) at least one substantially non-compliant sheath positioned over the non-preformed end of said expandable balloon such that said sheath is adjacent to one end of said stent without overlapping onto said stent, whereby radial expansion of the non-preformed end of the expandable balloon is constrained by the at least one substantially non-compliant sheath.

16. The balloon expandable stent-graft delivery system of claim 15 wherein said at least one sheath is affixed to said catheter.

17. The balloon expandable stent-graft delivery system of claim 15 wherein said sheath extends along a length of said catheter to the proximal end of said catheter such that it is slidably manipulative along said length of said catheter.

18. A method for introducing a stent-graft assembly into a blood vessel comprising the steps of:
   a) providing a balloon expandable stent-graft delivery system comprising:
      a catheter having proximal and distal ends thereof;
      an expandable balloon attached near the distal end of said catheter wherein said balloon comprises an interior surface, an exterior surface, and first and second ends, said first and second ends being substantially non-tapered upon expansion of said balloon from a first unexpanded diameter to a second larger diameter;
      a stent having an interior surface, an exterior surface, and first and second ends thereof wherein said stent is positioned around said expandable balloon;
      a graft having an interior surface, an exterior surface, and first and second ends thereof wherein said graft is positioned around said stent such that said stent is concentrically contained within said graft; and
      a substantially non-compliant sheath positioned over each of the first and second ends of said balloon such that each of the sheaths are adjacent to one of the first and second ends of the stent;
   b) inserting the balloon expandable stent-graft delivery system into the blood vessel;
   c) guiding the stent-graft assembly to a desired site;
   d) radially expanding a mid-portion of the expandable balloon to the second larger diameter while constraining at least one of the first and second ends of the balloon from radially expanding with the at least one substantially non-complaint sheath to seat the stent-graft assembly within the blood vessel at the desired site;
   e) deflating the balloon; and
   f) withdrawing the catheter and the expandable balloon from the blood vessel.

19. The method of claim 18 wherein the step of providing a stent-graft delivery system further comprises providing a stent-graft delivery system having one sheath positioned over each end of said balloon such that each of the sheaths are adjacent to one of the first and second ends of the stent, and the step of inflating the expandable balloon comprises radially expanding a mid-portion of the balloon while constraining both the first and second ends of the balloon with the sheaths.

20. The method of claim 18 wherein the step of providing a stent-graft delivery system further comprises providing a stent-graft delivery system wherein the first and second ends of the expandable balloon are invertedly attached to the catheter.

* * * * *

UNITED STATES PATENT AND TRADEMARK OFFICE
CERTIFICATE OF CORRECTION

PATENT NO.   : 5,522,882
DATED        : June 14, 1996
INVENTOR(S)  : Gaterud, et al It is certified that error appears in the above-indentified patent and that said Letters Patent is hereby corrected as shown below:

Column 1, Line 20, delete "Journal of Vascular and" and insert therefor --*Journal of Vascular and*--.

Column 8, Line 22, delete "stent-graff" and insert therefor --stent-graft--.

Signed and Sealed this

Seventh Day of January, 1997

Attest:

BRUCE LEHMAN

*Attesting Officer*    *Commissioner of Patents and Trademarks*